(12) United States Patent
Avery et al.

(10) Patent No.: US 10,682,467 B2
(45) Date of Patent: Jun. 16, 2020

(54) AUTOMATIC DRUG INJECTION DEVICE WITH TORSION DRIVE SPRING AND ROTATIONAL DOSE SETTING AND CORRECTION MECHANISM

(71) Applicant: Sanofi, Paris (FR)

(72) Inventors: Richard James Vincent Avery, Gloucestershire (GB); Matthew Jones, Warwick (GB)

(73) Assignee: Sanofi, Paris (FR)

( * ) Notice: Subject to any disclaimer, the term of this patent is extended or adjusted under 35 U.S.C. 154(b) by 261 days.

(21) Appl. No.: 15/517,817

(22) PCT Filed: Oct. 9, 2015

(86) PCT No.: PCT/EP2015/073435
§ 371 (c)(1),
(2) Date: Apr. 7, 2017

(87) PCT Pub. No.: WO2016/055629
PCT Pub. Date: Apr. 14, 2016

(65) Prior Publication Data
US 2017/0296754 A1    Oct. 19, 2017

(30) Foreign Application Priority Data
Oct. 9, 2014    (EP) .................................. 14306595

(51) Int. Cl.
*A61M 5/315*    (2006.01)
*A61M 5/20*    (2006.01)
*A61M 5/31*    (2006.01)

(52) U.S. Cl.
CPC .......... *A61M 5/31551* (2013.01); *A61M 5/20* (2013.01); *A61M 5/2033* (2013.01);
(Continued)

(58) Field of Classification Search
CPC .......... A61M 5/31551; A61M 5/31535; A61M 5/31541; A61M 5/31585
See application file for complete search history.

(56) References Cited

U.S. PATENT DOCUMENTS 7,955,303 B2    6/2011    Burren et al.
8,491,538 B2    7/2013    Kohlbrenner et al.
(Continued)

FOREIGN PATENT DOCUMENTS

CN    1509193    6/2004
EP    3089777 A1 *    11/2016    .............. A61M 5/20
(Continued)

OTHER PUBLICATIONS

Engineer's Edge LLC, Torsion Spring Constant Calculator and Formula, Accessed Apr. 17, 2019, https://www.engineersedge.com/spring_torsion_calc.htm (Year: 2000).*
(Continued)

*Primary Examiner* — Nathan R Price
*Assistant Examiner* — John A Doubrava
(74) *Attorney, Agent, or Firm* — Fish & Richardson P.C.

(57) ABSTRACT

The present disclosure is generally directed to a drug delivery device for selecting and dispensing a number of user variable doses of a medicament. The device comprises a housing, a dose selector operable to set a dose by rotation relative to the housing, a number sleeve arranged within the housing, a drive sleeve which is rotationally constrained to the housing during dose setting and dose correcting and which is rotatable relative to the housing during dose dispensing, a piston rod coupled to the housing and to the drive sleeve a drive spring arranged between the housing and the number sleeve, and a ratchet operatively arranged between the drive sleeve and the number sleeve. According to the disclosure the ratchet comprises at least one clicker
(Continued)

arm of one of the number sleeve and the drive sleeve and ratchet teeth of the other of the number sleeve and the drive sleeve.

18 Claims, 3 Drawing Sheets

(52) U.S. Cl.
CPC ...... *A61M 5/3157* (2013.01); *A61M 5/31535* (2013.01); *A61M 5/31541* (2013.01); *A61M 5/31553* (2013.01); *A61M 5/31583* (2013.01); *A61M 5/31593* (2013.01); *A61M 2005/202* (2013.01); *A61M 2005/3126* (2013.01); *A61M 2205/581* (2013.01); *A61M 2205/582* (2013.01); *A61M 2205/583* (2013.01); *A61M 2205/584* (2013.01)

(56) References Cited

U.S. PATENT DOCUMENTS

| | | |
|---|---|---|
| 2002/0120235 A1 | 8/2002 | Enggaard |
| 2005/0055011 A1* | 3/2005 | Enggaard .............. A61M 5/20 604/500 |
| 2008/0306445 A1 | 12/2008 | Burren et al. |
| 2009/0247951 A1 | 10/2009 | Kohlbrenner et al. |
| 2010/0274198 A1 | 10/2010 | Bechtold |
| 2011/0054412 A1* | 3/2011 | Eich .............. A61M 5/20 604/207 |
| 2012/0055011 A1 | 3/2012 | Tenne |
| 2012/0174658 A1 | 7/2012 | Gamel et al. |
| 2015/0100029 A1* | 4/2015 | Cowe .............. A61M 5/20 604/218 |
| 2016/0228651 A1* | 8/2016 | Plambech .............. A61M 5/20 |
| 2016/0317745 A1* | 11/2016 | Kjeldsen .............. A61M 5/20 |

FOREIGN PATENT DOCUMENTS

| | | | |
|---|---|---|---|
| JP | 2009-507581 | 2/2009 | |
| JP | 2010-503430 | 2/2010 | |
| JP | 2012-500067 | 1/2012 | |
| JP | 2012-506273 | 3/2012 | |
| JP | 2012-511358 | 5/2012 | |
| JP | 2016-533220 | 10/2016 | |
| WO | WO 2010/066796 | 6/2010 | |
| WO | WO 2011/043605 | 4/2011 | |
| WO | WO 2011/054412 | 5/2011 | |
| WO | WO 2013/167869 | 11/2013 | |
| WO | WO-2015101669 A1 * | 7/2015 | .............. A61M 5/20 |

OTHER PUBLICATIONS

International Preliminary Report on Patentability in International Application No. PCT/EP2015/073435, dated Apr. 11, 2017, 8 pages.
International Search Report and Written Opinion in International Application No. PCT/EP2015/073435, dated Dec. 12, 2015, 13 pages.

* cited by examiner

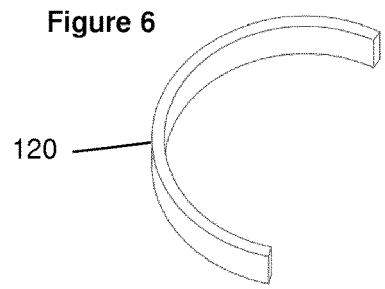
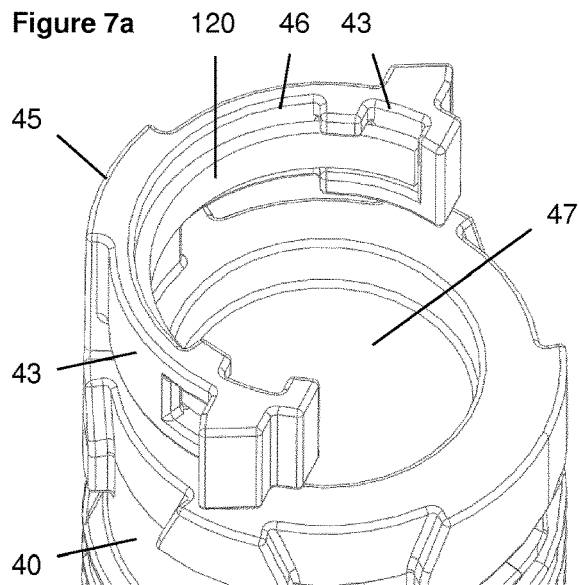
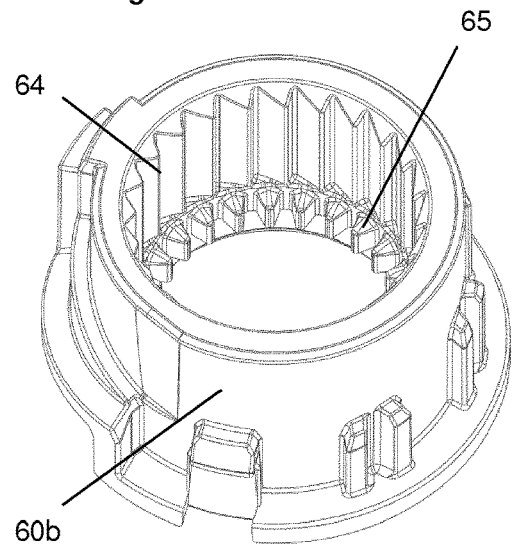
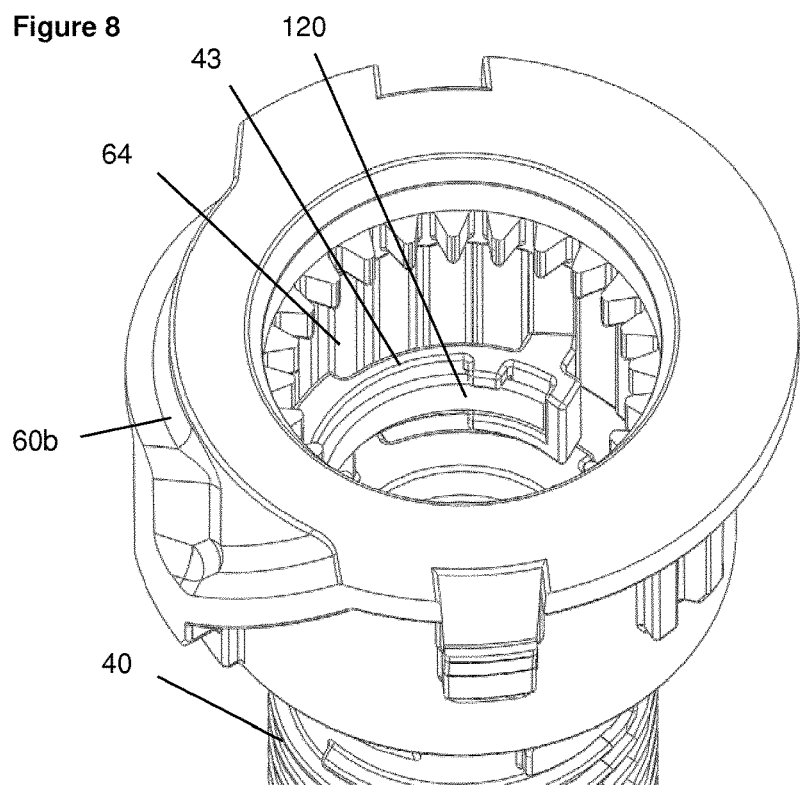

AUTOMATIC DRUG INJECTION DEVICE WITH TORSION DRIVE SPRING AND ROTATIONAL DOSE SETTING AND CORRECTION MECHANISM

CROSS-REFERENCE TO RELATED APPLICATIONS

This application is a U.S. national stage application under 35 USC § 371 of International Application No. PCT/EP2015/073435, filed on Oct. 9, 2015, which claims priority to European Patent Application No. 14306595.1 filed on Oct. 9, 2014, the entire contents of which are incorporated herein by reference.

TECHNICAL FIELD

The present disclosure is generally directed to a drug delivery device suitable for selecting and dispensing a number of user variable doses of a medicament. In more detail, the disclosure is directed to a drug delivery device comprising a housing, a dose selector operable to set a dose by rotation relative to the housing, a number sleeve arranged within the housing, a drive sleeve which is rotationally constrained to the housing during dose setting and dose correcting and which is rotatable relative to the housing during dose dispensing, a piston rod coupled to the housing and to the drive sleeve, a drive spring arranged between the housing and the number sleeve, and a ratchet clutch operatively arranged between the drive sleeve and the number sleeve.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. The present disclosure is not directed to so called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. Certain aspects of the present disclosure are applicable for both types of devices, i.e. for disposable devices as well as for reusable devices.

These types of pen delivery devices (so named because they often resemble an enlarged fountain pen) generally comprise three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

SUMMARY

In some devices a correction of an already set dose, i.e. reducing or dialling down the actually selected dose, is possible without dispensing the selected dose. EP 1 926 514 B1 discloses an injection device comprising a slipping clutch with a detent element of an actuation knob and a counter detent element of the device housing, which come into mutual positive and non-positive engagement in discrete latching positions of the device housing to arrest the actuation knob during a movement in the dosing direction or in the correction direction. In addition the device comprises a spring element, which applies a spring force opposing the movement of the actuation knob in one of the directions. The detent element and the counter detent element are formed in such a way, that they apply a lower resistance to the motion in one of the directions than in the other direction.

Further, WO 2010/046394 A1 discloses a dial mechanism for an injection device comprising a ring, which is rotationally constrained to the device housing during dose setting and which has a plurality of teeth having a steep edge in one direction and a sloped edge in the opposite direction. Due to this design of the teeth, a ratchet arm of a ratchet tube is allowed to rotate in one direction during dose setting which strains a torsion spring. In addition, this design of the teeth prevents the ratchet tube from rotating relative to the toothed ring in the opposite direction. This makes it impossible for the torsion spring to rotate back the ratchet tube. For dose correction the ratchet arm may be pulled out of engagement with the teeth by rotation of a reset tube. This results in rotation of the ratchet tube relative to the ring driven by the torsion spring. Due to the size of torque of the spring, the ratchet tube will move faster than the reset tube, such that the ratchet arm will flex to its initial position resulting in reengagement of the arm with the next steep tooth edge. The torque stored in the torsion spring may be released for dose dispensing by axially moving the ring out of engagement with the housing, whereby the torsion spring rotates back the ring, the ratchet tube and the reset tube.

Thus, the mechanism of WO 2010/046394 A1 requires an additional component part, namely the reset tube, to allow dose correction without dispensing medicament. This impedes the design of a compact and ergonomic device and further has economical drawbacks, especially for disposable devices.

Unpublished European Patent Application 13 16 3095 describes a drug delivery device for selecting and dispensing a number of user variable doses of a medicament as mentioned above. The ratchet clutch of this device comprises a clutch plate which is rotationally constrained to the number sleeve. The drive sleeve comprises at its proximal end face a ring of teeth engaging a corresponding ring of teeth arranged at a distal end face of the clutch plate.

Certain aspects of the present disclosure provide an alternative to the above solution. Certain aspects of the present disclosure provide a drug delivery device allowing dose correction without dispensing the selected dose.

The present disclosure provides an alternative to the ratchet between the drive sleeve and the number sleeve of unpublished European Patent Application 13 16 3095. In more detail, the ratchet according to the present disclosure comprises at least one clicker arm of one of the number sleeve and the drive sleeve and ratchet teeth of the other of the number sleeve and the drive sleeve. Thus, a separate clutch plate is not required. In addition, the construction of certain aspects of the present disclosure may allow withstanding higher torques, especially if the ratchet is arranged circumferentially, i.e. with the clicker arm and the ratchet teeth being arranged radially adjacently instead of an axially opposed arrangement of toothed rings.

The drive spring is arranged between the housing and the number sleeve. This includes embodiments where the spring is operatively connected to the housing and/or the number sleeve via a further component part, e.g. a nut directly coupled to the spring and driving the number sleeve.

The device may be a disposable device, i.e. a device which does not provide for an exchange of an empty cartridge.

According to a preferred embodiment, the at least one clicker arm deflects in a radial direction during relative rotation of the drive sleeve and the number sleeve. The clicker arm may be a cantilever extending in an axial direction or a cantilever extending in a circumferential direction. Alternatively, the clicker arm may be a beam extending in a circumferential direction and built-in at both ends.

Preferably, the drive spring is pre-strained, e.g. during assembly of the device, and is further strained (charged) during dose setting. For this purpose the number sleeve is rotatable relative to the housing between a first rotational end position, which is a minimum dose or at rest position with a dose of zero dialled, and a second rotational end position, which is the maximum dose position. In the first rotational end position the pre-strained drive spring exerts a first spring torque which is larger than zero to the number sleeve. In the second rotational end position the drive spring is fully strained and exerts a second spring torque which is larger than the first torque to the number sleeve.

According to the present disclosure, the ratchet is suitable to allow that the number sleeve is rotatable relative to the drive sleeve in a first direction by overcoming a first ratchet resistance torque and in a second, opposite direction by overcoming a second ratchet resistance torque which is larger than the first ratchet resistance torque and larger than the second spring torque. In other words, it is possible to overhaul the ratchet interface in both directions, however with a different resistance torque of the ratchet interface. This ratchet resistance torque is lower in the first dose setting (increasing) direction and higher in the opposite second dose correcting (reducing) direction. As the second ratchet resistance torque exceeds the torque exerted by the fully charged drive spring, the drive spring does not rewind the number sleeve after dose setting, while such a rotation is allowed if a user exerts an additional torque in the dose correcting direction. Hence, dose setting requires that a user rotates the number sleeve, e.g. via the dose selector, exerting a torque to overcome the first ratchet resistance torque and the increasing spring torque, while a user has to rotate the number sleeve in the opposite direction exerting a torque to overcome the second ratchet resistance torque assisted by the decreasing spring torque.

The at least one clicker arm of the ratchet interface is preferably an integral part of the drive sleeve. As an alternative, the clicker arm may be provided on the number sleeve. In a preferred embodiment two clicker arms are provided. The clicker arm may be a compliant cantilever or a beam built-in at both ends which is allowed to flex radially during overhauling of the ratchet interface. In an embodiment of the present disclosure, the at least one clicker arm is located radially inwards of the ratchet teeth. As a further alternative to a circumferential arm, the clicker arm may be an axial finger or the clicker arms could be replaced by a metal pressing that is rotationally constrained relative to the drive sleeve or number sleeve and that incorporates flexible arms to interact with the ratchet teeth. The ratchet teeth are preferably provided on the number sleeve, or (if the clicker arm is on the number sleeve) on the drive sleeve.

Preferably, the number sleeve is located within the housing such that at least a portion of the number sleeve, typically a portion provided with symbols like numbers, is visible through a first aperture or window or lens in the housing. In other words, the number sleeve is a component part which allows display of the actually set dose. The window or lens may be incorporated into the housing using a 'twin-shot' moulding technology. For example, the window or lens is moulded during a 'first shot' in a translucent material, and an outer cover of the housing is moulded during a 'second shot' in an opaque material.

In a preferred embodiment the drive sleeve is axially movable relative to the housing between a first axial position in which the drive sleeve is rotationally constrained to the housing for dose setting and dose correction and a second axial position in which the drive sleeve is rotatable relative to the housing for dose dispensing. Alternatively, the rotational coupling between the drive sleeve and the housing may be released by movement of a different component part. Preferably, the drive sleeve is partially or fully surrounded by the number sleeve.

The piston rod is preferably coupled to the housing and to the drive sleeve such that rotation of the drive sleeve relative to the housing causes the piston rod to translate relative to the housing. Thus, dose dispensing occurs if the drive sleeve is allowed to rotate driven by the drive spring. The coupling between the piston rod and the housing may be a threaded engagement and the coupling between the piston rod and the drive sleeve may be a splined interface allowing relative axial movement. The piston rod may be received in a central opening of the drive sleeve.

The resistance torque of the ratchet interface is generated by the at least one clicker arm and the ratchet teeth during disengaging. The resistance torque of the at least one clicker arm and the ratchet teeth is a function of the ramp angle (for example different ramped tooth angles during clockwise and anti-clockwise relative rotation), the friction coefficient and the mean radius of the at least one clicker arm and the ratchet teeth. Preferably, the ratchet features provide a detented position between the drive sleeve and the number sleeve corresponding to each dose unit.

For manufacturing and/or assembling reasons the number sleeve may comprise a number sleeve upper part and a number sleeve lower part which are rotationally and axially permanently constrained to each other after assembly of the device. For example, the number sleeve upper part may comprise the ratchet teeth, e.g. in the form of an inwardly directed toothed ring, or the at least one clicker arm while the number sleeve lower part may be provided with symbols at its outer surface. Although it is preferred that the drive sleeve is a single component part, the drive sleeve could be split into two parts with the part at the proximal end incorporating the ratchet features.

The compliant parts of the ratchet system need to provide sufficient torque without suffering from creep. This can be achieved if the device further comprises a ratchet spring in the form of a ring segment having a higher elastic modulus (Young's modulus) than the at least one clicker arm. This allows using plastic material for the drive sleeve and/or the number sleeve. Preferably, the ratchet spring is located such that the at least one clicker arm is biased in a radial direction towards the ratchet teeth. To accommodate and fix the ratchet spring, the at least one clicker arm may comprise a channel or groove in which the ratchet spring is received. This design allows a simple "open and shut" mould tooling, so reducing manufacturing costs. In a preferred embodiment the drive sleeve comprises two clicker arms which extend circumferentially in opposed directions from a web provided on one end of the drive sleeve with one single ratchet spring being held in an inwardly located groove extending over both clicker arms and the web.

The drug delivery device may further comprise a button operable to effect dose dispensing, for example by moving the drive sleeve via the button from its first axial position to its second axial position. The button is preferably a separate component part which is axially movable relative to the dose selector and may be splined to it. Further, the button may be rotationally coupled to the housing during dose dispensing to prevent rotation of the button and the dose selector. The button is a user operable element extending from the proximal end of the device and, preferably, does not change its axial position during dose setting. The button may be a multi-functional element and in addition to the above features may have a clicker feature, such as a dispense clicker.

The drive sleeve may comprise a distal end having clutch features for rotationally constraining the drive sleeve and the housing and an opposite proximal end having a bearing face for abutment of the button. The bearing face may be axially offset relative to the at least one clicker arm. Preferably, the bearing face is an inner web or inwardly directed flange which may be located distal of the at least one clicker arm.

A button spring may be provided axially interposed between the housing, preferably a web or flange of the housing, and the drive sleeve such that the drive sleeve is biased towards its first axial position, i.e. in the proximal direction. Due to the axial contact of the drive sleeve with the button via the bearing face, the button spring also pushes the button in the proximal direction. Thus, the drive sleeve is held by the button spring in its position coupled to the housing and the button and the drive sleeve may be axially displaced against the bias of the button spring.

The drug delivery device may comprise the housing, having the first aperture or window, the number sleeve positioned within the housing and rotatable with respect to the housing during dose setting and during dose dispensing, and a gauge element, which is interposed between the housing and the number sleeve. Preferably, the gauge element has a second aperture or window, which is positioned with respect to the first aperture or window of the housing such that at least a part of the number sleeve is visible through the first and second apertures or windows. The gauge element may be axially guided within the housing and in threaded engagement with the number sleeve such that rotation of the number sleeve causes an axial displacement of the gauge element.

The position of the gauge element may thus be used to identify the actually set and/or dispensed dose. Different colours of sections of the gauge member may facilitate identifying the set and/or dispensed dose without reading numbers, symbols or the like on a display. As the gauge element is in threaded engagement with the number sleeve, rotation of the number sleeve causes an axial displacement of the gauge element relative to the number sleeve and relative to the housing. The gauge element may have the form of a shield or strip extending in the longitudinal direction of the device. As an alternative, the gauge element may be a sleeve. In an embodiment of the disclosure, the number sleeve is marked with a sequence of numbers or symbols and the gauge element comprises an aperture. With the number sleeve located radially inwards of the gauge element, this allows that at least one of the numbers or symbols on the number sleeve is visible through the aperture. In other words, the gauge element may be used to shield or cover a portion of the number sleeve and to allow viewing only on a limited portion of the number sleeve. This function may be in addition to the gauge element itself being suitable for identifying or indicating the actually set and/or dispensed dose.

In a preferred embodiment, the number sleeve, during dose setting, is adapted to undergo a mere rotational movement within the housing and relative to the housing. In other words, the number sleeve does not perform a translational movement during dose setting. This prevents the need for the number sleeve to be wound out of the housing or for the housing to be prolonged for covering the number sleeve within the housing. Further, if the number sleeve is axially constrained within the housing the first rotational end position and the second rotational end position may be defined by corresponding rotational hard stops provided on the number sleeve and the gauge element. In other words, the drug delivery device comprises a limiter mechanism defining a maximum settable dose and a minimum settable dose. Typically, the minimum settable dose is zero (0 IU of insulin formulation), such that the limiter stops the device at the end of dose dispensing. The maximum settable dose, for example 60, 80 or 120 IU of insulin formulation, may be limited to reduce the risk of overdosage and to avoid the additional spring torque needed for dispensing very high doses, while still being suitable for a wide range of patients needing different dose sizes. The limiter mechanism may comprise a first rotational stop on the number sleeve and a first counter stop on the gauge element, which abut in the minimum dose (zero) position, and a second rotational stop on the number sleeve and a second counter stop on the gauge element, which abut in the maximum dose position. As the number sleeve rotates relative to the gauge element during dose setting and during dose dispensing, these two components are suitable to form a reliable and robust limiter mechanism.

The drug delivery device may further comprise a last dose protection mechanism for preventing the setting of a dose, which exceeds the amount of liquid left in a cartridge. This has the advantage that the user knows how much will be delivered before starting the dose delivery. It also ensures that dose delivery stops in a controlled manner without the bung entering the neck portion of the cartridge where the diameter is smaller which may result in an underdose. In a preferred embodiment, this last dose protection mechanism only detects the medicament remaining in the cartridge when the cartridge contains less than the maximum dose (e.g. 120 IU). For example, the last dose protection mechanism comprises a nut member interposed between the drive member and a component which rotates during dose setting and dose dispensing. The component which rotates during dose setting and dose dispensing may be the number sleeve or a dial sleeve rotationally constrained to the number sleeve. In a preferred embodiment, the number sleeve and/or a dial sleeve rotate during dose setting and during dose dispensing, whereas the drive member only rotates during dose dispensing together with the number sleeve and/or the dial sleeve. Thus, in this embodiment, the nut member will only move axially during dose setting and will remain stationary with respect to these components during dose dispensing. Preferably, the nut member is threaded to the drive member and splined to the number sleeve and/or the dial sleeve. As an alternative, the nut member may be threaded to the number sleeve and/or the dial sleeve and may be splined to the drive member. The nut member may be a full nut or a part thereof, e.g. a half nut.

A further aspect of the present disclosure is the provision of several interfaces on the axially movable drive sleeve. Preferably, the drive sleeve has a first interface for permanently rotationally constraining the drive sleeve and the lead screw. A second interface may be provided between the drive sleeve and the housing (or a housing component) for rotationally constraining the drive sleeve and the housing depending on the axial position of the drive sleeve. A third interface may be provided between the drive sleeve and the number sleeve (or a dose setting component) for rotationally constraining the drive sleeve and the number sleeve depending on the axial position of the drive sleeve. A fourth interface may be the ratchet interface. A fifth interface may be provided between the drive sleeve and the number sleeve or the gauge element for generating a feedback signal upon rotation of the drive sleeve, preferably only at the end of dose dispensing, and depending on the axial position of the drive sleeve.

Providing a resilient drive spring member, such as a torsion spring, generating the force or torque required for dose dispensing in a drug delivery device, reduces the user applied forces for dose dispensing. This is especially helpful for users with impaired dexterity. In addition, the dial extension of the known manually driven devices, which is a result of the required dispensing stroke, may be omitted by providing the resilient member because merely a small triggering stroke may be necessary for releasing the resilient member.

A drive spring according to the present disclosure preferably comprises at least one first coil formed from a helical wire and at least one second coil formed from a helical wire. The at least one first coil has a smaller pitch than the at least one second coil. In other words, the torsion spring is formed from a helical wire with at least two different pitches. In a first embodiment of the disclosure the smaller pitch is such that in the unstressed condition of the spring the respective coils are formed as 'closed' coils, i.e. the pitch equals the wire diameter and each coil contacts the adjacent coil, while the larger pitch portion has 'open' coils, i.e. the coils do not contact each other. The unstressed condition is a condition where no external load is applied to the spring, i.e. the spring is neither compressed nor extended nor distorted. Preferably, the spring has in its unstressed condition a uniform outer diameter. Having both open and closed coils in the spring has the following advantages: When used in a drug delivery device, the torsion spring is usually charged during dose setting. If all the coils were closed, winding up the spring would increase the length of the spring by one wire diameter for each turn, and so hook ends of the spring would no longer be aligned with their anchor points, which are e.g. on the number sleeve and the housing of the device. The open coils allow the spring to compress to accommodate the additional turns of wire, without increasing the total length of the spring. In addition, it is easier to manufacture the spring to a specified length if most of the coils are closed, as the length of these coils is only a function of the wire diameter.

Further, the open coils allow the spring to be compressed during assembly. For example, the spring is manufactured longer than the space available in the device. It is then compressed during assembly, ensuring that the axial positions of the hook ends are better aligned with their anchor points on the housing and the number sleeve. Including at least one open coil allows the spring to be compressed during assembly, which biases the number sleeve axially relative to the housing in a consistent direction, reducing the effects of geometric tolerances.

In a preferred embodiment the spring has a first end portion comprising at least one first coil, an opposite second end portion comprising at least one first coil and an intermediate portion comprising at least one second coil. Preferably, both ends are formed from 'closed' coils, i.e. the pitch equals the wire diameter and each coil contacts the adjacent coil, while the central portion has 'open' coils, i.e. the coils do not contact each other. As an alternative, the two opposite end portions may have a different pitch. The intermediate portion is not necessarily located in the geometrical middle of the spring, although this is a preferred embodiment. There may be more than one portion comprising at least one second coil. These portions may be spaced from each other by at least one portion having a first coil or at least one coil with a different pitch. The length of the portions may be substantially equal or may differ. For attachment of the spring to component parts of a drug delivery device the spring may have a hook at least at one of its ends, preferably at both ends. The addition of closed coils at each end makes the springs less prone to tangling with each other when they are stored together between manufacture and assembly. Further, closed coils at the ends provide a flat surface for contact with the housing and number sleeve which is preferred.

Features for generating a tactile and/or audible feedback during dose dispense, could be added between any component that rotates during dose dispense and any component that does not, e.g. between the number sleeve and the button.

In addition to the dispense clicker, a feedback signal may be provided during dose setting and/or dose correction. Such a signal is preferably provided by the ratchet interface of the drive sleeve and the number sleeve, wherein relative rotation of the number sleeve with respect to the drive sleeve during dose setting and/or dose correction generates an audible and/or tactile feedback signal. An audible click may be generated by re-engagement of the at least one clicker arm and the ratchet teeth. This feedback signal may be distinct from the dispense clicker signal.

A further feedback signal may be provided as an end of dose dispensing indication. Preferably, the drug delivery device further comprises a clicker arrangement having a clicker arm on the number sleeve, a ramp on the drive sleeve and a cam on a further element, e.g. the gauge element, wherein upon relative rotation of the number sleeve and the further element the clicker arm is elastically deflectable by the cam and relaxable upon disengagement with the cam thereby generating an audible and/or tactile feedback signal. When the drive sleeve is in a first axial position, the ramp preferably does not interact with the clicker arm which in turn prevents the clicker arm from contacting the cam, and when the drive sleeve is in a second axial position, the ramp deflects the clicker arm such that the clicker arm contacts the cam. The number sleeve and the further element may be in threaded engagement. Thus, the further element is axially displaced upon relative rotation of the number sleeve. This allows engagement and dis-engagement of the cam and the clicker arm depending on the relative axial position of the cam and the clicker arm.

With respect to the feedback signal generated at the end of dose dispensing, it is an important aspect of the present disclosure that the clicker arrangement comprises a first, rotatable element and a second, non-rotatable element with one of the first element and the second element comprising a clicker arm, which is elastically deformable, and the other of the first element and the second element comprising a cam. Upon relative rotation of the first element and the second element the clicker arm is elastically deflected by the cam and relaxes upon disengagement with the cam thereby generating an audible and/or tactile feedback signal. Certain aspects of the present disclosure include the idea of further providing a third, axially movable element having a ramp which interacts with the clicker arm at least in a defined position of the third element. In more detail, the ramp does not interact with the clicker arm which in turn prevents the clicker arm from contacting the cam when the third element is in a first axial position. However, when the third element is in a second axial position, the ramp deflects the clicker arm such that the clicker arm contacts the cam. In other words, the clicker arrangement may be activated to generate the feedback signal by bringing the third element in its second position and may be de-activated preventing generation of a signal by bringing the third element in its first position. This allows the feedback signal to be produced only in a defined mode, typically during dose dispensing when used in a drug delivery device. The feedback signal generated by the clicker arrangement is preferably distinct from other signals which may be generated in a drug delivery device, for example a visual indication and/or an audible and/or tactile feedback signal generated during dose setting, dose correction and/or dose dispensing.

According to the present disclosure, the cam preferably does not contact the clicker arm when the third element is in its first axial position, which is when used in a drug delivery device preferably if a trigger or actuation button is in a not depressed 'at rest' condition. Thus, during storage or dialling the clicker arm is not deflected and will not suffer creep deformation. In addition, the clicker arrangement does not cause friction losses during dialling or dose correction which contributes to a user-friendly device requiring only low dialling force or torque.

Preferably, the element comprising the clicker arm is a tubular element with the clicker arm being deflectable radially inwards and outwards. The third element comprising the ramp is preferably arranged radially inwards of the element comprising the clicker arm such that the ramp is able to push the clicker arm radially outwards. The element comprising the cam may be arranged radially outwards of the element comprising the clicker arm such that the cam is able to push the clicker arm radially inwards. In a preferred embodiment the first element is the number sleeve, the second element is the gauge element and the third element is the drive sleeve.

There are various ways of generating the audible and/or tactile feedback signal by any of the clicker arrangements of the present disclosure. For example, the audible and/or tactile feedback signal may be generated by disengagement of a clicker arm and a tooth or a cam. In other words, the signal is caused e.g. by the pre-tensioned clicker arm falling off an edge of the tooth or cam. As an alternative, the audible and/or tactile feedback signal may be generated by contact of a first portion of the clicker arm with the tooth or cam after disengagement of a second portion of the clicker arm with the tooth or cam. For example, the second portion of the clicker arm, e.g. a crank portion, may hit the tooth or cam after the first portion of the clicker arm, e.g. a projecting tip of the arm, disengages or loses contact with the tooth or cam. In an embodiment comprising a cam it is preferred if the element with the cam further comprises a recess for receiving the second portion, e.g. the tip, of the clicker arm after disengagement of the second portion of the clicker arm with the cam.

Preferably, the piston rod (lead screw) advances by a fixed displacement for each revolution of the drive sleeve. In other embodiments, the rate of displacement may vary. For example, the piston rod may advance a large displacement per revolution to dispense a first amount of medicament from the cartridge and then a smaller displacement per revolution to dispense the rest of the cartridge. This is advantageous, as it can compensate for the fact that the first dose dispensed from the cartridge often has a lower volume than other doses, for a given displacement of the mechanism. If the pitch is equal on the threads of the housing and the piston rod, the piston rod advances a fixed amount for every revolution of the movable sleeve. However, if in an alternative embodiment the first turn of the thread on the piston rod has a large pitch and the other turns have a small pitch, during the first revolution the piston rod displacement depends on the large pitch of the first turn of thread on the piston rod, so it displaces a large amount per revolution. For subsequent revolutions the piston rod displacement depends on the smaller pitch of the piston rod thread, so it displaces a smaller amount. If, in a further embodiment, the housing thread has a larger pitch than the piston rod, during the first revolution, the piston rod displacement depends on the pitch of the housing thread, so it displaces a large amount per revolution. For subsequent revolutions the piston rod displacement depends on the pitch of the piston rod thread, so it displaces a smaller amount.

The drug delivery device may comprise a cartridge containing a medicament. The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(0)14, Asp28] Exendin-4(1-39),
des Pro36 [Met(0)14, IsoAsp28] Exendin-4(1-39),
des Pro36 [Trp(02)25, Asp28] Exendin-4(1-39),
des Pro36 [Trp(02)25, IsoAsp28] Exendin-4(1-39),
des Pro36 [Met(0)14 Trp(02)25, Asp28] Exendin-4(1-39),
des Pro36 [Met(0)14 Trp(02)25, IsoAsp28] Exendin-4(1-39); or
des Pro36 [Asp28] Exendin-4(1-39),
des Pro36 [IsoAsp28] Exendin-4(1-39),
des Pro36 [Met(0)14, Asp28] Exendin-4(1-39),
des Pro36 [Met(0)14, IsoAsp28] Exendin-4(1-39),
des Pro36 [Trp(02)25, Asp28] Exendin-4(1-39),
des Pro36 [Trp(02)25, IsoAsp28] Exendin-4(1-39),
des Pro36 [Met(0)14 Trp(02)25, Asp28] Exendin-4(1-39),
des Pro36 [Met(0)14 Trp(02)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(02)25, Asp28] Exendin-4(1-39)-Lys6-NH2,
H-des Asp28 Pro36, Pro37, Pro38 [Trp(02)25] Exendin-4(1-39)-NH2,
H-(Lys)6-des Pro36, Pro37, Pro38 [Trp(02)25, Asp28] Exendin-4(1-39)-NH2,
H-Asn-(Glu)5-des Pro36, Pro37, Pro38 [Trp(02)25, Asp28] Exendin-4(1-39)-NH2,
des Pro36, Pro37, Pro38 [Trp(02)25, Asp28] Exendin-4(1-39)-(Lys)6-NH2,
H-(Lys)6-des Pro36, Pro37, Pro38 [Trp(02)25, Asp28] Exendin-4(1-39)-(Lys)6-NH2,
H-Asn-(Glu)5-des Pro36, Pro37, Pro38 [Trp(02)25, Asp28] Exendin-4(1-39)-(Lys)6-NH2,
H-(Lys)6-des Pro36 [Met(0)14, Asp28] Exendin-4(1-39)-Lys6-NH2,
des Met(0)14 Asp28 Pro36, Pro37, Pro38 Exendin-4(1-39)-NH2,
H-(Lys)6-desPro36, Pro37, Pro38 [Met(0)14, Asp28] Exendin-4(1-39)-NH2,
H-Asn-(Glu)5-des Pro36, Pro37, Pro38 [Met(0)14, Asp28] Exendin-4(1-39)-NH2,
des Pro36, Pro37, Pro38 [Met(0)14, Asp28] Exendin-4(1-39)-(Lys)6-NH2,
H-(Lys)6-des Pro36, Pro37, Pro38 [Met(0)14, Asp28] Exendin-4(1-39)-(Lys)6-NH2,
H-Asn-(Glu)5 des Pro36, Pro37, Pro38 [Met(0)14, Asp28] Exendin-4(1-39)-(Lys)6-NH2,
H-Lys6-des Pro36 [Met(0)14, Trp(02)25, Asp28] Exendin-4(1-39)-Lys6-NH2,
H-des Asp28 Pro36, Pro37, Pro38 [Met(0)14, Trp(02)25] Exendin-4(1-39)-NH2,
H-(Lys)6-des Pro36, Pro37, Pro38 [Met(0)14, Asp28] Exendin-4(1-39)-NH2,
H-Asn-(Glu)5-des Pro36, Pro37, Pro38 [Met(0)14, Trp (02)25, Asp28] Exendin-4(1-39)-NH2,
des Pro36, Pro37, Pro38 [Met(0)14, Trp(02)25, Asp28] Exendin-4(1-39)-(Lys)6-NH2,
H-(Lys)6-des Pro36, Pro37, Pro38 [Met(0)14, Trp(02)25, Asp28] Exendin-4(S1-39)-(Lys)6-NH2,
H-Asn-(Glu)5-des Pro36, Pro37, Pro38 [Met(0)14, Trp (02)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

Non-limiting, exemplary embodiments of the disclosure will now be described with reference to the accompanying drawings, in which:

FIG. 6 shows a ratchet spring of the device of FIG. 1;

FIGS. 7a, b show an interface between the number sleeve and the drive sleeve of the device of FIG. 1; and FIG. 8 shows the interface of FIGS. 7a, b.

DETAILED DESCRIPTION

Figure 1:
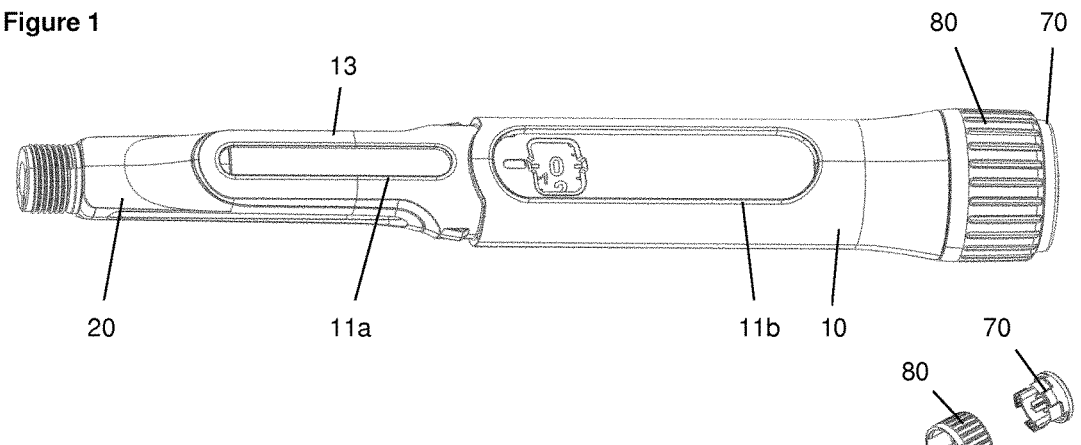
FIG. 1 shows a top view of the drug delivery device of the present disclosure in the minimum dose position.

FIG. 1 shows a drug delivery device in the form of an injection pen. The device has a distal end (left end in FIG.

Figure 2:
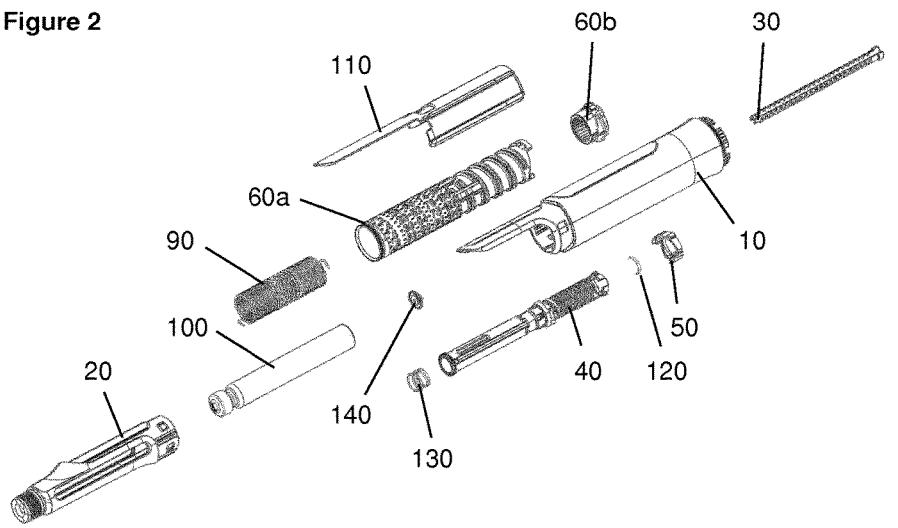
FIG. 2 shows an exploded view of the components of the device of FIG. 1.
Figure 3:
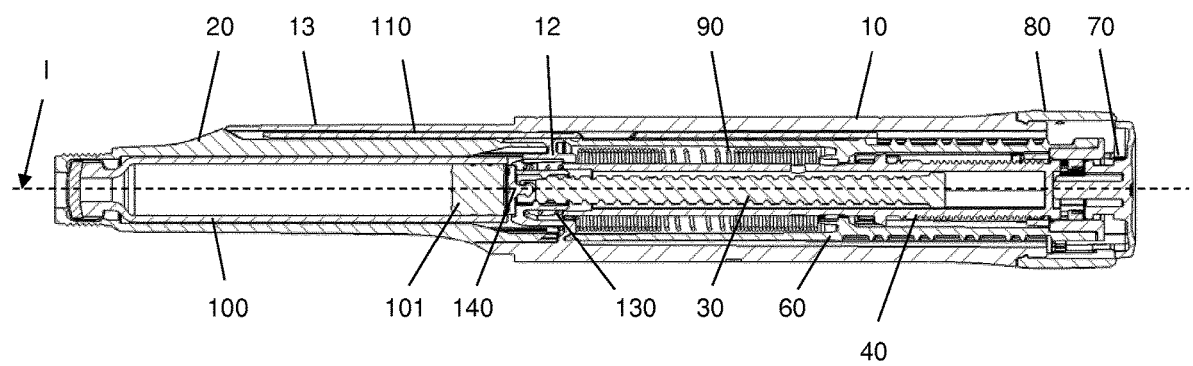
FIG. 3 shows a sectional view of the device of FIG. 1.

1) and a proximal end (right end in FIG. 1). The component parts of the drug delivery device are shown in FIG. 2. The drug delivery device comprises a body or housing 10, a cartridge holder 20, a lead screw (piston rod) 30, a drive sleeve 40, a nut 50, a number sleeve 60, a button 70, a dial grip or dose selector 80, a torsion spring 90, a cartridge 100, a gauge element 110, a ratchet spring 120, a button spring 130 and a bearing 140. A needle arrangement (not shown) with a needle hub and a needle cover may be provided as additional components, which can be exchanged as explained above. All components are located concentrically about a common principal axis I of the mechanism which is shown in FIG. 3.

The housing 10 or body is a generally tubular element having a proximal end with an enlarged diameter. The housing 10 provides location for the liquid medication cartridge 100 and cartridge holder 20, windows 11a, 11b for viewing the dose number on the number sleeve 60 and the gauge element 110, and a feature on its external surface, e.g. a circumferential groove, to axially retain the dose selector 80. A flange-like or cylindrical inner wall 12 comprises an inner thread engaging the piston rod 30. The housing 10 further has at least one internal, axially orientated slot or the like for axially guiding the gauge element 110. In the embodiment shown in the Figures, the distal end is provided with an axially extending strip 13 partly overlapping cartridge holder 20 and the gauge element 110. The Figures depict the housing 10 as a single housing component. However, the housing 10 could comprise two or more housing components which may be permanently attached to each other during assembly of the device.

The cartridge holder 20 is located at the distal side of housing 10 and permanently attached thereto. The cartridge holder may be a transparent or translucent component which is tubular to receive cartridge 100. The distal end of cartridge holder 20 may be provided with means for attaching a needle arrangement. A removable cap (not shown) may be provided to fit over the cartridge holder 20 and may be retained via clip features on the housing 10.

The piston rod 30 is rotationally constrained to the drive sleeve 40 via a splined interface. When rotated, the piston rod 30 is forced to move axially relative to the drive sleeve 40, through its threaded interface with the inner wall 12 of housing 10. The lead screw 30 is an elongate member with an outer thread 31 (FIG. 4a) engaging the corresponding thread of the inner wall 12 of housing 10. The thread 31 may have a large lead-in, for example a wedge shape form, at its distal end to engage a corresponding housing thread form on the first rotation. The interface comprises at least one longitudinal groove or track and a corresponding protrusion or spline of the driver 40. At its distal end, the lead screw 30 is provided with an interface for clip attachment of the bearing 140. In the present embodiment, this interface comprises two clip arms extending in the distal direction defining an insertion space between them for insertion of a bearing 140 interface. As an alternative, the interface may comprise only one single clip arm extending more than 180° about the longitudinal axis, or may comprise one or several clip arms. The clip arm(s) may have a bended form with a recessed clip portion. Preferably, the clip arm(s) form a cylindrical outer face having a diameter equal to or smaller than the outer diameter of the lead screw 30 at the base of the groove (flute base) of the outer thread 31. A concave contact surface is provided between the clip arms for abutment of a corresponding portion of bearing 140.

The drive sleeve 40 is a hollow member surrounding the lead screw 30 and arranged within number sleeve 60. It extends from an interface with the number sleeve 60 to the contact with the button spring 130. The drive sleeve 40 is axially movable relative to the housing 10, the piston rod 30 and the number sleeve 60 in the distal direction against the bias of button spring 130 and in the opposite proximal direction under the bias of button spring 130.

A splined tooth interface with the housing 10 prevents rotation of the drive sleeve 40 during dose setting. This interface comprises a ring of radially extending outer teeth 41 at the distal end of drive sleeve 40 and corresponding radially extending inner teeth 14 of the housing component 10. When the button 70 is pressed, these drive sleeve 40 to housing 10 spline teeth 14, 41 are disengaged allowing the drive sleeve 40 to rotate relative to housing 10.

A further splined tooth interface with the number sleeve 60 is not engaged during dialling, but engages when the button 70 is pressed, preventing relative rotation between the drive sleeve 40 and number sleeve 60 during dispense. In the embodiment shown in FIGS. 4a and 4b this interface comprises inwardly directed splines 61 on a flange 62 on the inner surface of the number sleeve 60 and a ring of radially extending outer splines 42 of drive sleeve 40. The corresponding splines 61, 42 are located on the number sleeve 60 and the drive sleeve 40, respectively, such that axial movement of the drive sleeve 40 relative to the (axially fixed) number sleeve 60 engages or disengages the splines to rotationally couple or decouple the drive sleeve 40 and the number sleeve 60.

Preferably, the splines 61, 42 are arranged such that they are decoupled when teeth 41 of drive sleeve 40 and inner teeth 14 of housing component 10 mesh and engage when teeth 41 and inner teeth 14 disengage. In a preferred embodiment the splines 61, 42 are longer in the axial direction compared with teeth 41, 14. This allows engagement of the splines 61, 42 shortly before disengagement of teeth 41, 14. In other words, the splines 61, 42 and the teeth 41, 14 are designed and arranged such that actuation of the button 70 rotationally constrains the drive sleeve 40 to the number sleeve 60 before the drive sleeve 40 is allowed to rotate relative to housing 10. Similarly, as the button 70 is released after dose dispensing axial movement of the drive sleeve 40 first rotationally constrains the drive sleeve 40 to the housing and thereafter decouples splines 61, 42. As an alternative to the corresponding splines 61, 42 teeth may be provided.

A fourth interface of the drive sleeve 40 which is shown in FIGS. 7a to 8 in more detail comprises two clicker arms 43 located at the proximal end of drive sleeve 40 and a ring of ratchet teeth 64 of number sleeve 60.

The driver 40 has a threaded section 44 providing a helical track for the nut 50. In addition, a last dose abutment or stop is provided which may be the end of the thread 44 track or preferably a rotational hard stop for interaction with a corresponding last dose stop of nut 50, thus limiting movement of the nut 50 on the thread 44. At least one longitudinal spline engages a corresponding track of the lead screw 30.

As shown in FIG. 7a in more detail, the proximal end of drive sleeve 40 is provided with a web 45. The clicker arms 43 extend circumferentially in opposite directions of web 45 as cantilevers. The free end of each clicker arm 43 is provided with an outwardly directed tip with different ramp angles in the clockwise and the counter clockwise direction. A groove 46 extends on the inner side of drive sleeve 40 from one clicker arm 43 over the web 45 to the other clicker arm 43. This groove 46 holds ratchet spring 120 which biases the clicker arms 43 radially outwards if they are deflected radially inwards. Further, the drive sleeve is provided with a bearing face 47 in the form of an inner wall located distally of the clicker arms 43.

The last dose nut 50 is located between the number sleeve 60 and the drive sleeve 40. It is rotationally constrained to the number sleeve 60, via a splined interface. It moves along a helical path relative to the drive sleeve 40, via a threaded interface (thread 44), when relative rotation occurs between the number sleeve 60 and drive sleeve 40 which is during dialling only. As an alternative, the nut 50 may be splined to the driver 40 and threaded to the number sleeve 60. In the embodiment shown in the Figures, the nut 50 is a full nut, but in alternative embodiments it may be a half nut, i.e. a component extending approximately 180° around the center axis of the device. As a further alternative, if the driver 40 was formed from two separate components that became rigidly engaged during assembly then the nut 50 could also be a complete nut. A last dose stop is provided engaging stop of drive sleeve 40 when a dose is set corresponding to the remaining dispensable amount of medicament in the cartridge 100.

The dose indicator or number sleeve 60 is a tubular element as shown in FIGS. 2 and 3. The number sleeve 60 is rotated during dose setting (via dose selector 80) and dose correction and during dose dispensing by torsion spring 90. Together with gauge element 110 the number sleeve 60 defines a zero position ('at rest') and a maximum dose position. Thus, the number sleeve 60 may also be seen as a dose setting member.

For manufacturing reasons the number sleeve 60 of the embodiment shown in the Figures comprises a number sleeve lower 60a which is rigidly fixed to a number sleeve upper 60b during assembly to form the number sleeve 60. Number sleeve lower 60a and number sleeve upper 60b are separate components only to simplify number sleeve 60 mould tooling and assembly. As an alternative, the number sleeve 60 may be a unitary component. The number sleeve 60 is constrained to the housing 10 by features towards the distal end to allow rotation but not translation. The number sleeve lower 60a is marked with a sequence of numbers, which are visible through the gauge element 110 and the window 11b in the housing 10, to denote the dialled dose of medicament. Further, the number sleeve lower 60a has a portion with an outer thread 63 engaging the gauge element 110. End stops are provided at the opposite ends of thread 63 to limit relative movement with respect to the gauge element 110.

Figure 5A:
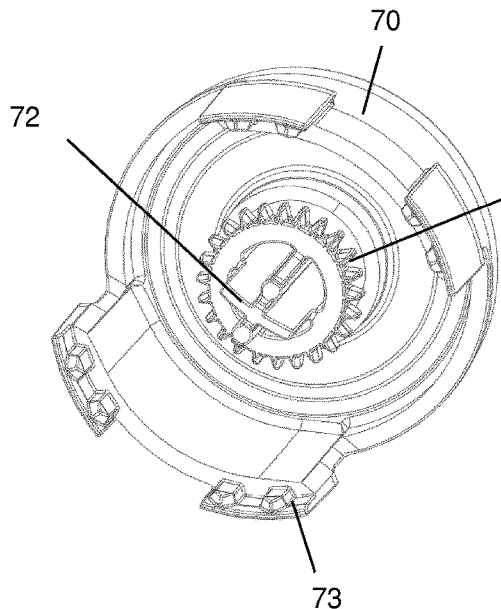
FIGS. 5a, b show an interface between the button and the number sleeve of the device of FIG. 1.
Figure 5B:
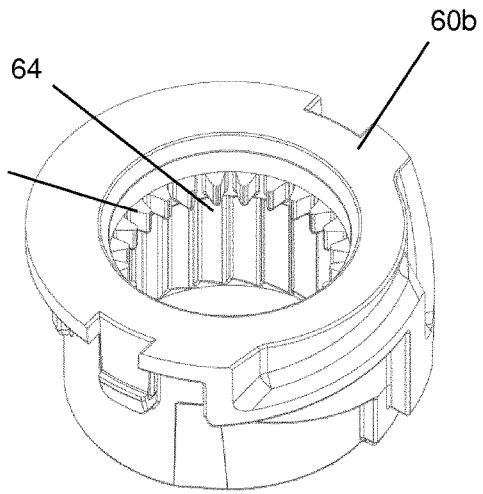

An inner surface of the number sleeve upper 60b is provided with a ring of ratchet teeth 64. As shown in FIGS. 5b and 7b ratchet teeth 64 have different ramp angles in the clockwise and the counter clockwise direction corresponding to the ramp angles of the tip of clicker arm 43.

This ratchet provides a detented position between the number sleeve and drive sleeve corresponding to each dose unit, and engages the different ramped tooth angles during clockwise and anti-clockwise relative rotation. In addition, clutch features which have the form of a ring of splines 65 in the embodiment of FIG. 5b are provided inwardly directed on number sleeve upper 60b for engagement with splines 71 of the button 70 during dose setting and dose correction.

An interface for attachment of the torsion spring 90 to the number sleeve lower 60a comprises large lead-ins and a groove feature with a pocket or anchor point for receiving a first coil or hook portion of the spring. The groove has an end feature in the form of a ramp that is in interference with the hook portion of the spring. The design of the groove is such that the spring 90 may be received within the pocket without interfering with the gauge element 110.

The button 70 which forms the proximal end of the device is permanently splined to the dose selector 80. A central stem 72 extends distally from the proximal actuation face of the button 70. The stem 72 is provided with the splines 71 for engagement with splines 65 of the number sleeve upper 60b (FIG. 5a). Button 70 is rotationally constrained via splines 65, 71 to the number sleeve upper 60b when the button 70 is not pressed, but this spline interface is disconnected when the button 70 is pressed. The button 70 has a discontinuous annular skirt with further splines 73. When the button 70 is pressed, splines 73 on the button 70 engage with splines on the housing 10, preventing rotation of the button 70 (and hence the dose selector 80) during dispense. These splines 73 disengage when the button 70 is released, allowing a dose to be dialled.

The dose selector 80 is axially constrained to the housing 10. It is rotationally constrained, via the splined interface, to the button 70. This splined interface which includes grooves interacting with spline features formed by the annular skirt of button 70 remains engaged irrespective of the dose button 70 axial positions. The dose selector 80 or dose dial grip is a sleeve-like component with a serrated outer skirt.

Figure 4A:
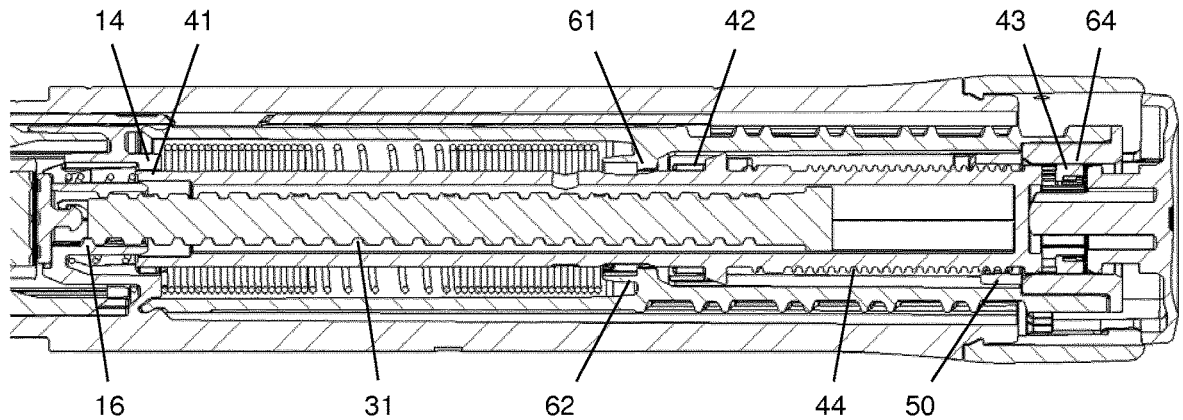
FIG. 4a shows an enlarged sectional view of a detail of the device of FIG. 1 in the dose setting mode.
Figure 4B:
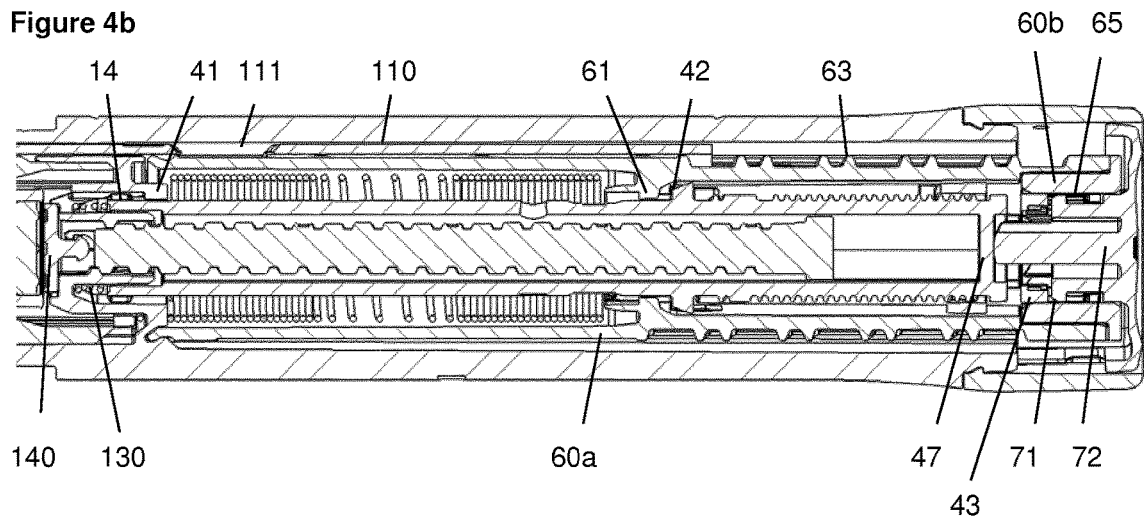
FIG. 4b shows an enlarged sectional view of a detail of the device of FIG. 1 in the dose dispensing mode.

The drive spring 90 is a torsion spring attached at its distal end to the housing 10 and at the other end to the number sleeve 60. The torsion spring 90 is located inside the number sleeve 60 and surrounds a distal portion of the drive sleeve 40. The spring has a hook at one end for attachment on the number sleeve 60. A similar hook end is provided at the opposite end for attachment on the housing 10. The torsion spring 90 is pre-wound upon assembly, such that it applies a torque to the number sleeve 60 when the mechanism is at zero units dialled. The action of rotating the dose selector 80, to set a dose, rotates the number sleeve 60 relative to the housing 10, and charges the torsion spring 90 further. The torsion spring 90 is formed from a helical wire with at least two different pitches. In FIGS. 4a and 4b both ends are formed from 'closed' coils, i.e. the pitch equals the wire diameter and each coil contacts the adjacent coil. The central portion has 'open' coils, i.e. the coils do not contact each other.

The cartridge 100 is received in cartridge holder 20 (FIG. 3). The cartridge 100 may be a glass ampoule having a moveable rubber bung 101 at its proximal end. The distal end of cartridge 100 is provided with a pierceable rubber seal which is held in place by a crimped annular metal band. In the embodiment depicted in the Figures, the cartridge 100 is a standard 1.5 ml cartridge. The device is designed to be disposable in that the cartridge 100 cannot be replaced by the user or health care professional. However, a reusable variant of the device could be provided by making the cartridge holder 20 removable and allowing backwinding of the lead screw 30 and the resetting of nut 50.

The gauge element 110 is constrained to prevent rotation but allow translation relative to the housing 10 via a splined interface. The gauge element 110 has a helical feature on its inner surface which engages with the helical thread cut in the number sleeve 60 such that rotation of the number sleeve 60 causes axial translation of the gauge element 110. This helical feature on the gauge element 110 also creates stop abutments against the end of the helical cut in the number sleeve 60 to limit the minimum and maximum dose that can be set. The gauge element 110 is a window element which has a generally plate or band like component having a central aperture 111 or window and two flanges extending on either side of the aperture. The flanges are preferably not transparent and thus shield or cover the number sleeve 60, whereas the aperture 111 or window allows viewing a portion of the number sleeve lower 60a. Further, gauge element 110 may have a cam and a recess interacting with a clicker arm (not shown) of the number sleeve 60 at the end of dose dispensing.

As can be seen in FIG. 6 the ratchet spring 120 has the form of a ring segment. It may be curved metal plate having a higher stiffness compared with clicker arms 43.

The button spring 130 is a compression spring. The axial position of the drive sleeve 40, ratchet spring 120 and button 70 is defined by the action of the button spring 130, which applies a force on the drive sleeve 40 in the proximal direction. This spring force is reacted via the drive sleeve 40 and button 70, and when 'at rest' it is further reacted through the dose selector 80 to the housing 10. In the 'at rest' position, it ensures that the button splines 71 are engaged with the number sleeve splines 65, and the drive sleeve teeth 41 are engaged with teeth 14 of the housing 10.

The bearing 140 is axially constrained to the piston rod 30 and acts on the bung 101 within the liquid medicament cartridge. It is axially clipped to the lead screw 30, but free to rotate. The bearing 140 comprises a disc having a stem extending in the proximal direction. The stem has at its proximal end a convex contact surface. In addition, a recessed portion may be provided on the stem. The curvature of the convex contact surface and the concave contact surface of the piston rod is chosen such that the contact diameter between the bearing 140 and lead screw 30 is small to minimize the frictional losses at this interface. The design of the clip interface between bearing 140 and lead screw 30 permits the lead screw 30 to be assembled axially, from the proximal end and through the thread engagement to the housing 10, which simplifies assembly. In addition, this design allows a simple "open and shut" mould tooling for both components.

With the device in the 'at rest' condition as shown in FIG. 4a, the number sleeve 60 is positioned against its zero dose abutment with the gauge element 110 and the button 70 is not depressed. Dose marking '0' on the number sleeve 60 is visible through the windows 11b and 111 of the housing 10 and gauge element 110, respectively.

The torsion spring 90, which has a number of pre-wound turns applied to it during assembly of the device, applies a torque to the number sleeve 60 and is prevented from rotating by the zero dose abutment. It may also be possible to 'back-wind' the mechanism slightly due to an offset between the zero dose stop and the angular offset of the drive sleeve spline teeth. This has the effect of preventing possible weepage when a dose is dialled and the zero dose abutment is disengaged.

The automated assembly of the torsion spring 90 into the number sleeve 60 can be achieved by incorporating large lead-ins and a groove feature to the number sleeve 60. As the torsion spring 90 is rotated during assembly, the hook end form locates in the groove feature before engaging the anchor point in the number sleeve 60. To help to prevent the torsion spring 90 disengaging the anchor point during subsequent assembly steps it is possible to create an interference between the torsion spring 90 and the number sleeve 60, or a one-way clip feature.

The user selects a variable dose of liquid medicament by rotating the dial grip or dose selector 80 clockwise, which generates an identical rotation in the number sleeve 60 via the splined interfaces between the dial grip 80 and the button 70 and between the button 70 and number sleeve upper 60b. The window 11b in the housing 10 and the window 111 of the gauge component 110 allow the user to view the set dose number on the number sleeve lower 60a.

The drive sleeve 40 is prevented from rotating as the dose is set and the number sleeve 60 rotated, due to the engagement of its splined teeth 41 with the teeth 14 of housing 10. Relative rotation therefore occurs between the drive sleeve 40 and the number sleeve 60, causing the ratchet 43, 64 to slip.

The user torque required to rotate the dial grip 80 is a sum of the torque required to wind up the drive spring 90, and the torque required to overhaul the ratchet feature 43, 64. The clicker arms 43 on the drive sleeve 40 are forced radially outwards by the ratchet spring 120 and into engagement with the teeth 64 on the number sleeve upper 60b. The torque required to overhaul the ratchet in the dose set direction is a function of the radial force supplied by the ratchet spring 120, the clockwise ramp angle of the ratchet 43, 64, the friction coefficient between the mating surfaces and the mean radius of the ratchet features 43, 64.

As the user rotates the dial grip 80 sufficiently to increment the mechanism by 1 increment, the number sleeve 60 rotates relative to the drive sleeve 40 by 1 ratchet tooth 64. At this point the ratchet teeth 64 re-engage into the next detented position. An audible click is generated by the ratchet re-engagement, and tactile feedback is given by the change in torque input required.

With no user torque applied to the dial grip, the number sleeve 60 is now prevented from rotating back under the torque applied by the drive spring 90, solely by the ratchet engagement 43, 64 between the drive sleeve and the number sleeve upper. The torque necessary to overhaul the ratchet 43, 64 in the anti-clockwise direction is a function of the radial force applied by the ratchet spring 120, the anti-clockwise ramp angle of the ratchet 43, 64, the friction coefficient between the mating surfaces and the mean radius of the ratchet features. The torque necessary to overhaul the ratchet 43, 64 must be greater than the torque applied to the number sleeve 60 by the drive spring 90. The ratchet ramp angle is therefore increased in the anti-clockwise direction to ensure this is the case whilst ensuring the dial-up torque is as low as possible.

The user may now choose to increase the selected dose by continuing to rotate the dial grip 80 in the clockwise direction. The process of overhauling the ratchet interfaces 43, 64 between the number sleeve 60 and drive sleeve 40 is repeated for each dose increment. Additional energy is stored within the drive spring 90 for each dose increment and audible and tactile feedback is provided for each increment dialled by the re-engagement of the ratchet teeth 64 with clicker arms 43. The torque required to rotate the dial grip 80 increases as the torque required to wind up the drive spring 90 increases. The torque required to overhaul the ratchet in the anti-clockwise direction must therefore be greater than the torque applied to the number sleeve by the torsion spring when the maximum dose has been reached.

With the mechanism in a state in which a dose has been selected, the user is able to deselect (correct) any number of increments from this dose. Deselecting a dose is achieved by the user rotating the dial grip 80 anti-clockwise. The torque applied to the dial grip 80 by the user is sufficient, when combined with the torque applied by the drive spring 90, to overhaul the ratchet 43, 64 between the drive sleeve 40 and number sleeve upper 60b in the anti-clockwise direction. When the ratchet 43, 64 is overhauled, anti-clockwise rotation occurs in the number sleeve 60 returning it towards the zero dose position, and unwinding the drive spring 90.

With the mechanism in a state in which a dose has been selected, the user is able to activate the mechanism to commence delivery of a dose. Delivery of a dose is initiated by the user depressing the button 70 axially as shown in FIG. 4b.

The drive sleeve 40 travels axially with the button 70. The splined tooth interface 42, 61 rotationally constrains the drive sleeve 40 to the number sleeve lower 60a. The splined tooth interface 14, 41 between the drive sleeve and the housing 10 disengages, so the drive sleeve 40 can now rotate and is driven by the drive spring 90 via the number sleeve 60, the ratchet 43, 64 between the number sleeve upper and the drive sleeve and via splines 42, 61 between the number sleeve lower and the drive sleeve. Rotation of the drive sleeve 40 causes the piston rod 30 to rotate due to their splined engagement, and the piston rod 30 then advances due to its threaded engagement to the housing 10.

Delivery of a dose continues via the mechanical interactions described above while the user continues to depress the button 70. If the user releases the button 70, the button spring 130 returns the drive sleeve to its 'at rest' position (together with the button), engaging the splines 14, 41 between the drive sleeve and housing, preventing further rotation and stopping dose delivery.

Once the delivery of a dose is stopped, by the number sleeve 60 returning to its zero dose position, the user may release the button 70, which will re-engage the spline teeth 14, 41 between the drive sleeve 40 and housing 10. The mechanism is now returned to the 'at rest' condition.

Although two clicker arms 43 are shown on the drive sleeve 40, there could be one or many. The clicker arms 43 are shown as cantilevers, but could be replaced by beams that are built-in at both ends. Any number of axial fingers at the end of the drive sleeve 40 could be used instead of the circumferential clicker arms 43. The ratchet spring 120 may not be necessary, if any compliant parts of the ratchet system provide sufficient torque and do not suffer from creep. The clicker arms 43 on the drive sleeve 40 could be replaced by a metal pressing that is rotationally constrained relative to the drive sleeve and that incorporates flexible arms to interact with the teeth on the number sleeve upper 60b. The drive sleeve 40 could be split into two parts with the part at the proximal end incorporating the ratchet features 43 and/or the bearing face 47 for the button 70. Although there is no tactile or audible feedback during dose dispense in the depicted embodiment, it could be added between any component that rotates during dose dispense and any component that does not, e.g. between the number sleeve upper 60b and the button 70.

| Reference Numerals: | |
| --- | --- |
| 10 | housing |
| 11a, b | opening |
| 12 | flange-like inner wall |
| 13 | strip |
| 14 | teeth |
| 20 | cartridge holder |
| 30 | lead screw (piston rod) |
| 31 | outer thread |
| 40 | drive sleeve |
| 41 | teeth |
| 42 | spline |
| 43 | clicker arm |
| 44 | threaded section |
| 45 | web |
| 46 | groove |
| 47 | bearing face |

| Reference Numerals: | |
| --- | --- |
| 50 | nut |
| 60 | number sleeve |
| 60a | number sleeve lower |
| 60b | number sleeve upper |
| 61 | spline |
| 62 | flange |
| 63 | outer thread |
| 64 | ratchet tooth |
| 65 | spline |
| 70 | button |
| 71 | spline |
| 72 | stem |
| 73 | spline |
| 80 | dose selector |
| 90 | drive spring (torsion spring) |
| 100 | cartridge |
| 101 | bung |
| 110 | gauge element |
| 111 | aperture |
| 120 | ratchet spring |
| 130 | button spring |
| 140 | bearing |
| 1 | longitudinal axis |

The invention claimed is:

1. A drug delivery device for selecting and dispensing a number of user variable doses of a medicament, comprising:
   a housing,
   a dose selector configured to set a dose by rotation relative to the housing,
   a number sleeve arranged within the housing and comprising a number sleeve upper part and a number sleeve lower part which are rotationally and axially permanently constrained to each other,
   a drive sleeve configured to be rotationally constrained to the housing during dose setting and dose correcting and configured to be rotatable relative to the housing during dose dispensing,
   a piston rod coupled to the housing and to the drive sleeve,
   a drive spring arranged between the housing and the number sleeve, and
   a ratchet configured to have a first ratchet resistance torque corresponding to a first ratchet resistance direction and a second ratchet resistance torque corresponding to a second ratchet resistance direction,
   wherein the first ratchet resistance torque is different than the second ratchet resistance torque and the first ratchet resistance direction is different than the second ratchet resistance direction,
   wherein the ratchet is operatively arranged between the drive sleeve and the number sleeve,
   wherein the ratchet comprises at least one clicker arm of one of the number sleeve or the drive sleeve and ratchet teeth of the other of the number sleeve or the drive sleeve,
   wherein the at least one clicker arm and the ratchet teeth are arranged radially adjacent one another with the at least one clicker arm deflecting in a radial direction during relative rotation of the drive sleeve and the number sleeve, and
   wherein the number sleeve upper part comprises the ratchet teeth or the at least one clicker arm, and the number sleeve lower part comprises symbols on its outer surface.

2. The drug delivery device according to claim 1, wherein the number sleeve is configured to rotate relative to the housing between a first rotational end position, in which the drive spring exerts a first spring torque which is larger than zero to the number sleeve, and a second rotational end position, in which the drive spring exerts a second spring torque which is larger than the first spring torque to the number sleeve, and wherein the number sleeve is configured to rotate relative to the drive sleeve in the first ratchet resistance direction by overcoming the first ratchet resistance torque and rotatable relative to the drive sleeve in the second ratchet resistance direction by overcoming the second ratchet resistance torque which is larger than the first ratchet resistance torque and larger than the second spring torque.

3. The drug delivery device according to claim 1, wherein the first ratchet resistance torque is a function of a ramp angle, a friction coefficient and a mean radius of the at least one clicker arm and the ratchet teeth.

4. The drug delivery device according to claim 1, comprising a ratchet spring in the form of a ring segment having a higher elastic modulus than an elastic modulus of the at least one clicker arm, wherein the ratchet spring is located such that the at least one clicker arm is biased in a radial direction at least during relative rotation of the drive sleeve and the number sleeve.

5. The drug delivery device according to claim 1, comprising a button configured to effect dose dispensing.

6. The drug delivery device according to claim 1, comprising a gauge element interposed between the housing and the number sleeve, the housing having a first aperture, wherein the gauge element has a second aperture positioned with respect to the first aperture of the housing such that at least a part of the number sleeve is visible through the first and second apertures, and wherein the gauge element is axially guided within the housing and in threaded engagement with the number sleeve such that rotation of the number sleeve causes an axial displacement of the gauge element.

7. The drug delivery device according to claim 1, wherein the drive sleeve comprises:

a first interface configured to permanently rotationally constrain the drive sleeve and the piston rod, a second interface configured to rotationally constrain the drive sleeve and the housing depending on the axial position of the drive sleeve, a third interface configured to rotationally constrain the drive sleeve and the number sleeve depending on the axial position of the drive sleeve, and a fourth interface comprising the ratchet.

8. The drug delivery device according to claim 1, wherein the drive spring comprises at least one first coil formed from a first portion of a helical wire and at least one second coil formed from a second portion of the helical wire, with the at least one first coil having a smaller pitch than the at least one second coil.

9. The drug delivery device according to claim 1, further comprising a cartridge containing a medicament.

10. The drug delivery device according to claim 4, wherein the at least one clicker arm comprises a channel or groove configured to receive the ratchet spring.

11. The drug delivery device according to claim 5, wherein the drive sleeve is axially movable relative to the housing between a first axial dose setting and dose correcting position and a second axial dose dispensing position, and comprises a distal end having clutch features configured to rotationally constrain the drive sleeve and the housing, and an opposite proximal end having a bearing face for abutment of the button.

12. The drug delivery device according to claim 11, comprising a button spring axially interposed between the housing and the drive sleeve such that the drive sleeve is biased towards the first axial position.

13. The drug delivery device according to claim 6, wherein the number sleeve is axially constrained within the housing and wherein the first rotational end position and the second rotational end position are defined by corresponding rotational hard stops provided on the number sleeve and the gauge element.

14. The drug delivery device according to claim 8, wherein the drive spring has a first end portion comprising at least one coil of a first coil type, an opposite second end portion comprising at least one coil of the first coil type and an intermediate portion comprising at least one coil of a second coil type.

15. The drug delivery device of claim 9, where the medicament comprises a pharmaceutically active compound.

16. A drug delivery device for selecting and dispensing a number of user variable doses of a medicament, comprising a housing, a dose selector configured to set a dose by rotation relative to the housing, a number sleeve arranged within the housing, a drive sleeve configured to be rotationally constrained to the housing during dose setting and dose correcting and configured to be rotatable relative to the housing during dose dispensing, a piston rod coupled to the housing and to the drive sleeve, a drive spring arranged between the housing and the number sleeve, a ratchet configured to have a first ratchet resistance torque corresponding to a first ratchet resistance direction and a second ratchet resistance torque corresponding to a second ratchet resistance direction, wherein:

the first ratchet resistance torque is different than the second ratchet resistance torque and the first ratchet resistance direction is different than the second ratchet resistance direction, the ratchet is operatively arranged between the drive sleeve and the number sleeve, the ratchet comprises at least one clicker arm of one of the number sleeve or the drive sleeve and ratchet teeth of the other of the number sleeve or the drive sleeve, and the at least one clicker arm and the ratchet teeth are arranged radially adjacent one another with the at least one clicker arm deflecting in a radial direction during relative rotation of the drive sleeve and the number sleeve, and a ratchet spring comprising a ring segment having a higher elastic modulus than an elastic modulus of the at least one clicker arm, wherein the ratchet spring is located such that the at least one clicker arm is biased in a radial direction at least during relative rotation of the drive sleeve and the number sleeve.

17. A drug delivery device for selecting and dispensing a number of user variable doses of a medicament, comprising:

a housing having a first aperture, a dose selector configured to set a dose by rotation relative to the housing, a number sleeve arranged within the housing, a drive sleeve configured to be rotationally constrained to the housing during dose setting and dose correcting and configured to be rotatable relative to the housing during dose dispensing, a piston rod coupled to the housing and to the drive sleeve,
a drive spring arranged between the housing and the number sleeve,
a ratchet configured to have a first ratchet resistance torque corresponding to a first ratchet resistance direction and a second ratchet resistance torque corresponding to a second ratchet resistance direction, wherein:
   the first ratchet resistance torque is different than the second ratchet resistance torque and the first ratchet resistance direction is different than the second ratchet resistance direction,
   the ratchet is operatively arranged between the drive sleeve and the number sleeve,
   the ratchet comprises at least one clicker arm of one of the number sleeve or the drive sleeve and ratchet teeth of the other of the number sleeve or the drive sleeve, and
   the at least one clicker arm and the ratchet teeth are arranged radially adjacent one another with the at least one clicker arm deflecting in a radial direction during relative rotation of the drive sleeve and the number sleeve, and
a gauge element interposed between the housing and the number sleeve, wherein:
   the gauge element has a second aperture positioned with respect to the first aperture of the housing such that at least a part of the number sleeve is visible through the first and second apertures, and
   the gauge element is axially guided within the housing and in threaded engagement with the number sleeve such that rotation of the number sleeve causes an axial displacement of the gauge element.

18. A drug delivery device for selecting and dispensing a number of user variable doses of a medicament, comprising:
a housing,
a dose selector configured to set a dose by rotation relative to the housing,
a number sleeve arranged within the housing,
a drive sleeve configured to be rotationally constrained to the housing during dose setting and dose correcting and configured to be rotatable relative to the housing during dose dispensing,
a piston rod coupled to the housing and to the drive sleeve,
a drive spring arranged between the housing and the number sleeve,
a ratchet configured to have a first ratchet resistance torque corresponding to a first ratchet resistance direction and a second ratchet resistance torque corresponding to a second ratchet resistance direction, wherein:
   the first ratchet resistance torque is different than the second ratchet resistance torque and the first ratchet resistance direction is different than the second ratchet resistance direction,
   the ratchet is operatively arranged between the drive sleeve and the number sleeve,
   the ratchet comprises at least one clicker arm of one of the number sleeve or the drive sleeve and ratchet teeth of the other of the number sleeve or the drive sleeve,
   the at least one clicker arm and the ratchet teeth are arranged radially adjacent one another with the at least one clicker arm deflecting in a radial direction during relative rotation of the drive sleeve and the number sleeve, and
the drive sleeve comprises:
   a first interface configured to permanently rotationally constrain the drive sleeve and the piston rod,
   a second interface configured to rotationally constrain the drive sleeve and the housing depending on the axial position of the drive sleeve,
   a third interface configured to rotationally constrain the drive sleeve and the number sleeve depending on the axial position of the drive sleeve, and
   a fourth interface comprising the ratchet.

\* \* \* \* \*